US007105331B2

(12) United States Patent
Bowman

(10) Patent No.: US 7,105,331 B2
(45) Date of Patent: *Sep. 12, 2006

(54) ICE/CED-3 LIKE PROTEASE DESIGNATED FMH-1

(75) Inventor: Michael R. Bowman, Westwood, MA (US)

(73) Assignee: Genetics Institute, LLC, Cambridge, MA (US)

(*) Notice: Subject to any disclaimer, the term of this patent is extended or adjusted under 35 U.S.C. 154(b) by 226 days.

This patent is subject to a terminal disclaimer.

(21) Appl. No.: 10/439,676

(22) Filed: May 16, 2003

(65) Prior Publication Data
US 2003/0180935 A1 Sep. 25, 2003

Related U.S. Application Data

(63) Continuation of application No. 09/962,834, filed on Sep. 25, 2001, now Pat. No. 6,586,225, which is a continuation of application No. 08/675,123, filed on Jul. 3, 1996, now abandoned.

(51) Int. Cl.
C12N 9/50 (2006.01)
(52) U.S. Cl. .................. 435/219; 435/226; 530/350
(58) Field of Classification Search ............... 530/300; 435/212, 219, 226; 536/23.2, 23.5
See application file for complete search history.

(56) References Cited

U.S. PATENT DOCUMENTS

| 4,235,871 A | 11/1980 | Papahadjopoulos et al. ..... 424/450 |
| 4,501,728 A | 2/1985 | Geho et al. .................. 424/450 |
| 4,737,323 A | 4/1988 | Martin et al. ................. 264/4.3 |
| 4,837,028 A | 6/1989 | Allen ......................... 424/450 |
| 5,264,618 A | 11/1993 | Felgner et al. ............... 560/224 |
| 5,459,127 A | 10/1995 | Felgner et al. .................. 514/7 |
| 5,786,173 A * | 7/1998 | Alnemri et al. ............. 435/69.1 |
| 6,586,225 B1 * | 7/2003 | Bowman .................... 435/226 |

FOREIGN PATENT DOCUMENTS

| WO | WO 89/01973 A2 | 3/1989 |
| WO | WO 90/11092 A1 | 10/1990 |
| WO | WO 90/14074 A1 | 11/1990 |
| WO | WO 91/16024 A1 | 10/1991 |
| WO | WO 93/14778 A1 | 8/1993 |
| WO | WO 93/19183 A1 | 9/1993 |
| WO | WO 94/16716 A1 | 8/1994 |
| WO | WO 95/20660 A2 | 8/1995 |
| WO | WO95026718 A1 | 10/1995 |
| WO | WO 96/00297 A1 | 1/1996 |
| WO | WO 96/10038 A1 | 4/1996 |
| WO | WO 97/35020 A1 | 9/1997 |

OTHER PUBLICATIONS

Boldin, M. et al., "Involvement of MACH, a Novel MORT1.FADD-Interacting Protease, in Fas/APO-1- and TNF Receptor-Induced Cell Death", Cell (Jun. 14, 1996) 803-815, 85(6), Cell Press.

Boldin, M. et al., "Self-association of the "Death Domains" of the p55 Tumor Necrosis Factor (TNF) Fas/APO1 prompts signaling for TNF and Fas/APO1 effects," Journal of Biological Chemistry (Jan. 6, 1995) 387-391, 270(1), American Society for Biochemistry and Molecular Biology.

Chinnaiyan, A. et al., FADD, "a novel death domain-containing protein, interacts with the death domain of Fas and initiates apoptosis", Cell (May 19, 1995) 505-512, 81(4), Cell Press.

Duan, H. et al., "ICE-LAP6, a Novel Member of the ICE/Ced-3 Gene Family, Is Activated by the Cytotoxic T Cell Protease Granzyme B," Journal of Biological Chemistry, (Jul. 12, 1996), 16720-16724, 271(28), American Society for Biochemistry and Molecular Biology.

Faucheu, C. et al., "A novel human protease similar to the interleukin-1 beta converting enzyme induces apoptosis in transfected cells", EMBO Journal (May 1, 1995) 1914-1922, 14(9), European Molecular Biology Organization.

Fernandes-Alnemri, T. et al., "In vitro activation of CPP32 and Mch3 by Mch4, a novel human apoptotic cysteine protease containing two FADD-like domains", PNAS (Jul. 23, 1996) 7464-7469, 93(15), National Academy of Sciences.

Fernandes-Alnemri, T. et al., "Mch2, a new member of the apoptotic Ced-3/Ice cysteine protease gene family", Cancer Research (Jul. 1, 1995) 2737-2742, 55(13), American Association for Cancer Research.

Fernandes-Alnemri, T. et al., "Mch3, a novel human apoptotic cysteine protease highly related to CPP32", Cancer Research (Dec. 15, 1995) 6045-6052, 55(24), American Association for Cancer Research.

Fraser, A. and Evan, G., "A License to Kill," Cell (Jun. 14, 1996), 781-784, 85(6), Cell Press.

Hillier, L. et al. "The Washu-Merck EST Project;" EMBL/Genbanc Accession No. T96912; Sequence Reference HS91272 (Apr. 14, 1995).

Hsu, H., "The TNF Receptor 1-Associated Protein TRADD Signals Cell Death and NF-KB Activation," Cell, (May 19, 1995), 495-504, 81(4), Cell press.

(Continued)

Primary Examiner—Nashaat T. Nashed
(74) Attorney, Agent, or Firm—Kirkpatrick & Lockhart Nicholson Graham LLP

(57) ABSTRACT

Polynucleotides encoding novel proteases designated "FMH-1" are disclosed. Host cells transformed with such polynucleotides and methods for making FMH-1 proteases are also disclosed. The invention also provides FMH-1 proteases and antibodies that react with them, along with pharmaceutical compositions comprising FMH-1 proteases or polynucleotides encoding FMH-1 proteases. Methods for treating conditions associated with excessive or insufficient apoptosis by administering such pharmaceutical compositions are also disclosed.

1 Claim, No Drawings

OTHER PUBLICATIONS

Kumar, S. et al., "Induction of apoptosis by the mouse Nedd2 gene, which encodes a protein similar to the product of the Caenorhabditis elegans cell death gene ced-3 and the mammalian IL-1 beta-converting enzyme", *Genes & Development* (Jul. 15, 1994) 1613-1626, 8(14). Cold Spring Harbor Laboratory Press.

Muzio, M. et al., "FLICE, A Novel FADD-Homologous ICE/CED-3-like Protease, Is Recruited to the CD95 (Fas/APO-1) Death-Inducing Signaling Complex", Cell, 817-827 (Jun. 14, 1996), 85(6), Cell Press.

Nicholson, D., "ICE/CED3-like Proteases as Therapeutic Targets for the Control of Inappropriate Apoptosis", *Nature Biotechnology* (Mar. 1996) 297-301, 14(3), Nature America Inc.

Vincenz, C. and Dixit, V., "Fas-associated Death Domain Protein Interleukin-1 Beta-converting Enzyme 2(FLICE2), an ICE/Ced-3 Homologue, Is Proximally Involved in CD95- and p55-mediated Death Signaling", *Journal of Biological Chemistry* (Mar. 7, 1997) 6578-6583, 272(10), American Society for Biochemistry and Molecular Biology.

Fernandes-Alnemri, T. et al., CPP32, a novel human apoptotic protein with homology to *Caenorhabditis elegans* cell death protein Ced-3 and mammalian interleukin-1β-converting enzyme, *J. Biol. Chem.*, 269(49):30761-30764, 14.

Kamens, J. et al., Identification and characterization of ICH-2, a novel member of the interleukin-1β-converting enzyme family of cysteine proteases, *J. Biol. Chem.*, 270(25):15250-15256, 1995.

Kaufman, R. J., Selection and coamplification of heterologous genes in mammalian cells, *Methods Enzymol.*, 185:537-566, 1990.

Kaufman, R. J. et al, Improved vectors for stable expression of foreign genes in mammalian cells by use of the untranslated leader sequence from EMC virus, *Nucleic Acids Res.*, 19(16):4485-4490, 1991.

Krstenansky, J. L. and Mao, S. J. T., Antithrombin properties of C-terminus of hirudin using synthetic unsulfated $N^{\alpha}$-acetyl-hirudin$_{45-65}$, *FEBS Lett.*, 211(1):10-16, 1987.

Kumar, S. et al., Identification of a set of genes with developmentally down-regulated expression in the mouse brain, *Biochem. Biophys. Res. Commun.*, 185(3):1155-1161, 1992.

Merrifield, R. B., Solid phase peptide synthesis. I. The synthesis of a tetrapeptide, *J. Amer. Chem. Soc.*, 85(14):2149-2154, 1963.

Munday, N. A. et al., Molecular cloning and pro-apoptotic activity of ICE$_{rel}$II and ICE$_{rel}$III, members of the ICE/CED-3 family of cysteine proteases, *J. Biol. Chem.*, 270(26):15870-15876, 1995.

Summers, M D. and Smith, G E., A manual of methods for baculovirus vectors and insect cell culture procedures, *Texas Agricultural Experiment Station Bulletin*, 1555 College Station, Texas, Texas A & M University; 1987.

Wang, L. et al., *Ich-1*, an *Ice/ced-3*-related gene, encodes both positive and negative regulators of programmed cell death, *Cell*, 78(5):739-750, 1994.

\* cited by examiner

```
SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1704 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 121..1683

(xi) SEQUENCE DESCRIPTION: SEQ ID NO: 1:

CCCGGGCAGG TCTTGGAGCA CACAGAGGAT TCTACTTTCT TTAAAACTTT GTTTTCAGGC      60

AATTTCCCTG AGAACCGTTT ACTTCCAGAA GATTGGTGGA GCTTGATCTG AAGGCTGGCC     120

ATGAAATCTC AAGGTCAACA TTGGTATTCC AGTTCAGATA AAAACTGTAA AGTGAGCTTT     180

CGTGAGAAGC TTCTGATTAT TGATTCAAAC CTGGGGGTCC AAGATGTGGA GAACCTCAAG     240

TTTCTCTGCA TAGGATTGGT CCCCAACAAG AAGCTGGAGA AGTCCAGCTC AGCCTCGGAT     300

GTTTTTGAAC ATCTCTTGGC AGAGGATCTG CTGAGTGAGG AAGACCCTTT CTTCCTGGCA     360

GAACTCCTCT ATATCATACG GCAGAAGAAG CTGCTGCAGC ACCTCAACTG TACCAAAGAG     420

GAAGTGGAGC GACTGCTGCC CACCCGACAA AGGGTTTCTC TGTTTAGAAA CCTGCTCTAC     480

GAACTGTCAG AAGGCATTGA CTCAGAGAAC TTAAAGGACA TGATCTTCCT TCTGAAAGAC     540

TCGCTTCCCA AAACTGAAAT GACCTCCCTA AGTTTCCTGG CATTTCTAGA GAAACAAGGT     600

AAAATAGATG AAGATAATCT GACATGCCTG GAGGACCTCT GCAAAACAGT TGTACCTAAA     660

CTTTTGAGAA ACATAGAGAA ATACAAAAGA GAGAAAGCTA TCCAGATAGT GACACCTCCT     720

GTAGACAAGG AAGCCGAGTC GTATCAAGGA GAGGAAGAAC TAGTTTCCCA AACAGATGTT     780

AAGACATTCT TGGAAGCCTT ACCGCAGGAG TCCTGGCAAA ATAAGCATGC AGGTAGTAAT     840

GGTAACAGAG CCACAAATGG TGCACCAAGC CTGGTCTCCA GGGGGATGCA AGGAGCATCT     900

GCTAACACTC TAAACTCTGA AACCAGCACA AAGAGGGCAG CTGTGTACAG GATGAATCGG     960

AACCACAGAG GCCTCTGTGT CATTGTCAAC AACCACAGCT TTACCTCCCT GAAGGACAGA    1020

CAAGGAACCC ATAAAGATGC TGAGATCCTG AGTCATGTGT TCCAGTGGCT TGGGTTCACA    1080
```

-continued

```
GTGCATATAC ACAATAATGT GACGAAAGTG GAAATGGAGA TGGTCCTGCA GAAGCAGAAG    1140

TGCAATCCAG CCCATGCCGA CGGGGACTGC TTCGTGTTCT GTATTCTGAC CCATGGGAGA    1200

TTTGGAGCTG TCTACTCTTC GGATGAGGCC CTCATTCCCA TTCGGAGAT CATGTCTCAC     1260

TTCACAGCCC TGCAGTGCCC TAGACTGGCT GAAAAACCTA AACTCTTTTT CATCCAGGCC    1320

TGCCAAGGTG AAGAGATACA GCCTTCCGTA TCCATCGAAG CAGATGCTCT GAACCCTGAG    1380

CAGGCACCCA CTTCCCTGCA GGACAGTATT CCTGCCGAGG CTGACTTCCT ACTTGGTCTG    1440

GCCACTGTCC CAGGCTATGT ATCCTTTCGG CATGTGGAGG AAGGCAGCTG GTATATTCAG    1500

TCTCTGTGTA ATCATCTGAA GAAATTGGTC CCAAGGATGC TGAAATTTCT GGAAAAGACA    1560

ATGGAAATCA GGGCAGGAA GAGAACAGTG TGGGGTGCTA AACAGATCTC AGCAACCTCC     1620

CTGCCCACGG CCATCTCTGC GCAGACACCT CGACCCCCCA TGCGCAGGTG GAGCAGCGTT    1680

TCCTAGTTCT TTCCAGAGGC TTCC                                           1704
```

(2) INFORMATION FOR SEQ ID NO: 2:

(i) SEQUENCE CHARACTERISTICS:
        (A) LENGTH: 521 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 2:

```
Met Lys Ser Gln Gly Gln His Trp Tyr Ser Ser Asp Lys Asn Cys
1               5                   10                  15

Lys Val Ser Phe Arg Glu Lys Leu Leu Ile Ile Asp Ser Asn Leu Gly
            20                  25                  30

Val Gln Asp Val Glu Asn Leu Lys Phe Leu Cys Ile Gly Leu Val Pro
        35                  40                  45

Asn Lys Lys Leu Glu Lys Ser Ser Ala Ser Asp Val Phe Glu His
    50                  55                  60

Leu Leu Ala Glu Asp Leu Leu Ser Glu Glu Asp Pro Phe Phe Leu Ala
65                  70                  75                  80

Glu Leu Leu Tyr Ile Ile Arg Gln Lys Lys Leu Leu Gln His Leu Asn
                85                  90                  95

Cys Thr Lys Glu Glu Val Glu Arg Leu Leu Pro Thr Arg Gln Arg Val
            100                 105                 110

Ser Leu Phe Arg Asn Leu Leu Tyr Glu Leu Ser Glu Gly Ile Asp Ser
        115                 120                 125

Glu Asn Leu Lys Asp Met Ile Phe Leu Leu Lys Asp Ser Leu Pro Lys
    130                 135                 140

Thr Glu Met Thr Ser Leu Ser Phe Leu Ala Phe Leu Glu Lys Gln Gly
145                 150                 155                 160

Lys Ile Asp Glu Asp Asn Leu Thr Cys Leu Glu Asp Leu Cys Lys Thr
                165                 170                 175

Val Val Pro Lys Leu Leu Arg Asn Ile Glu Lys Tyr Lys Arg Glu Lys
            180                 185                 190

Ala Ile Gln Ile Val Thr Pro Pro Val Asp Lys Glu Ala Glu Ser Tyr
        195                 200                 205

Gln Gly Glu Glu Glu Leu Val Ser Gln Thr Asp Val Lys Thr Phe Leu
    210                 215                 220

Glu Ala Leu Pro Gln Glu Ser Trp Gln Asn Lys His Ala Gly Ser Asn
225                 230                 235                 240
```

-continued

```
Gly Asn Arg Ala Thr Asn Gly Ala Pro Ser Leu Val Ser Arg Gly Met
            245                 250                 255

Gln Gly Ala Ser Ala Asn Thr Leu Asn Ser Glu Thr Ser Thr Lys Arg
            260                 265                 270

Ala Ala Val Tyr Arg Met Asn Arg Asn His Arg Gly Leu Cys Val Ile
            275                 280                 285

Val Asn Asn His Ser Phe Thr Ser Leu Lys Asp Arg Gln Gly Thr His
            290                 295                 300

Lys Asp Ala Glu Ile Leu Ser His Val Phe Gln Trp Leu Gly Phe Thr
305                 310                 315                 320

Val His Ile His Asn Asn Val Thr Lys Val Glu Met Glu Met Val Leu
            325                 330                 335

Gln Lys Gln Lys Cys Asn Pro Ala His Ala Asp Gly Asp Cys Phe Val
            340                 345                 350

Phe Cys Ile Leu Thr His Gly Arg Phe Gly Ala Val Tyr Ser Ser Asp
            355                 360                 365

Glu Ala Leu Ile Pro Ile Arg Glu Ile Met Ser His Phe Thr Ala Leu
    370                 375                 380

Gln Cys Pro Arg Leu Ala Glu Lys Pro Lys Leu Phe Phe Ile Gln Ala
385                 390                 395                 400

Cys Gln Gly Glu Glu Ile Gln Pro Ser Val Ser Ile Glu Ala Asp Ala
            405                 410                 415

Leu Asn Pro Glu Gln Ala Pro Thr Ser Leu Gln Asp Ser Ile Pro Ala
            420                 425                 430

Glu Ala Asp Phe Leu Leu Gly Leu Ala Thr Val Pro Gly Tyr Val Ser
            435                 440                 445

Phe Arg His Val Glu Glu Gly Ser Trp Tyr Ile Gln Ser Leu Cys Asn
    450                 455                 460

His Leu Lys Lys Leu Val Pro Arg Met Leu Lys Phe Leu Glu Lys Thr
465                 470                 475                 480

Met Glu Ile Arg Gly Arg Lys Arg Thr Val Trp Gly Ala Lys Gln Ile
            485                 490                 495

Ser Ala Thr Ser Leu Pro Thr Ala Ile Ser Ala Gln Thr Pro Arg Pro
            500                 505                 510

Pro Met Arg Arg Trp Ser Ser Val Ser
            515                 520
```

ICE/CED-3 LIKE PROTEASE DESIGNATED FMH-1

CROSS-REFERENCE TO RELATED APPLICATIONS

This is a continuation of application(s) application Ser. No. 09/962,834 filed on Sep. 25, 2001, now U.S. Pat. No. 6,586,225 which is a continuation of Ser. No. 08/675,123 filed on Jul. 3, 1996 now abandoned.

FIELD OF THE INVENTION

The present invention relates to protease proteins, nucleic acids encoding such proteins, and methods of treatment using such proteins and polynucleotides.

BACKGROUND OF THE INVENTION

Complex multicellular organisms employ numerous mechanisms to protect and maintain the integrity of cellular components from which they are comprised. In the event of questionable or irreparable cell damage, one seemingly drastic measure available to a compromised cell is to commit suicide and to discretely remove itself for the altruistic benefit of the organism as a whole. Cell suicide is triggered in response to pathogenic invasion (such as by a virus) to halt the spread to neighboring cells, but it also occurs under nonthreatening conditions to replace redundant or unnecessary cells, as occurs in tissue morphogenesis and remodeling, and in the normal turnover of cells that occurs when they have exhausted their overall usefulness within the organism. Nicholson, Nature Biotechnology 14:297 (1996).

The pathological manifestation of cell suicide, known as "apoptosis", occurs as a result of a highly systematic and deliberate cell death pathway. These types of cell deaths have been appropriately termed "physiological cell death", where in addition to this suicide pathway, death occurs in specific cells at a predetermined time. Apoptotic death is a highly ordered process that is characterized by nuclear changes such as chromatin condensation, fragmentation and margination as well as internucleosomal DNA cleavage (usually resulting in the hallmark DNA laddering), and by ultrastructural changes including cytoskeletal disruption, cell shrinkage and membrane blebbing which then leads to fragmentation of the dying cell into numerous membrane-bound apoptotic bodies that are subsequently engulfed by neighboring cells or professional macrophages in the final resolution of the suicide process. Apoptotic suicide has many advantages over other forms of cell death, owing principally to the membrane integrity that is maintained throughout the entire process. Necrotic cells, for example, leak their constituents into the surrounding extracellular space usually resulting in an inflammatory response. Nicholson, supra.

The recent explosion in interest in apoptosis is warranted given the substantial evidence that inappropriate apoptosis may contribute to the pathology of several human diseases (including without limitation neurological diseases, such as Alzheimer's disease, amyotrophic lateral sclerosis, spinal muscular atrophy, neurological stroke damage, Parkinson's disease and Huntington's disease; immune system disorders, such as autoimmune syndromes, AIDS and type I diabetes; cardiovascular conditions, such as ischemic cardiac damage; proliferative conditions, such as solid tumors, lymphomas (such as follicular lymphoma) and leukemias; and others, such as pathogenic (including viral) infections, alopecia and aging. These can be divided into disorders of excessive apoptosis (such as neurodegenerative disease or ischemic damage) and those where insufficient apoptosis occurs (such as autoimmune syndromes, cancers and sustained pathogenic infections). Nicholson, supra.

In contrast to the above mentioned disorders, insufficient apoptosis is also associated with several human diseases. For example, many cancers are now believed to be the consequence of failed apoptotic cell death instead of enhanced cell growth as was originally thought. Two gene defects that are highly associated with proliferative disorders (p53 and Bcl-2) are now known to be regulators of the apoptotic process. Another example of flawed apoptosis is in autoimmune disorders where the failure to remove autoreactive lymphocytes that arise during development, or subsequent to an immune response, occurs. One form of autoimmune disease, lupus erythematosus, may involve failure to complete apoptosis execution since most lupus autoantibodies recognize cryptic epitopes within a distinct subset of polypeptides that are proteolytic cleavage victims in the cell death pathway. Finally, persistent viral infections may be sustained and propagated because the normal host cell suicide response that would be engaged following viral infection is cleverly suppressed by antiapoptotic viral gene products. Nicholson, supra.

Many of the clues which have implicated various components of the cell death pathway have arisen from disease association, genetic analysis and in vitro reconstitution of apoptotic events. Collectively, this information has helped define a biochemical pathway that accounts for many of the key events that occur in dying cells in vivo. Many parts of this pathway, particularly those involved in the effector events that mediate the actual cell death process itself, appear to be common to most cell types. At the heart of this process, proteases related to mammalian interleukin-1β converting enzyme (ICE) and to nematode CED-3 appear to play an essential role. Several of the substrates that are cleaved by ICE/CED-3 like proteases at the onset of apoptosis have also been identified. These include proteins that function in DNA repair as well as structural proteins and regulatory enzymes. A fundamental principle of apoptotic cell death thus appears to be the proteolytic disabling of key homeostatic- and repair-processes as well as the obvious structural dismantling of the cell that is required to facilitate its breakdown and subsequent packaging into apoptotic bodies. Moreover, ICE/CED-3 like proteolytic activities have been demonstrated to play a role in most if not all of these cleavage events. Nicholson, supra.

Molecular cloning has identified several human homologues of ICE and CED-3 including $ICE_{rel}$-II (TX, ICH-2), $ICE_{rel}$-III, ICH-1, CPP32 (apopain, Yama) Mch2 and Mch3 (ICE-LAP3) (Munday et al., J. Biol. Chem. 270:15870 (1995); Faucheu et al., EMBO J. 14:1914 (1995); Kamens et al., J. Biol. Chem. 270:15250 (1995); Kumar et al., Biochem. Biophys. Res. Commun. 185:1155 (1992); Kumar et al., Genes and Develop. 8:1613 (1994); Wang et al., Cell 78:739 (1994); Fernandes-Alnemri et al., J. Biol. Chem. 269:30761 (1994); Fernandes-Alnemri et al., Cancer Res. 55:2737 (1995); Fernandes-Alnemri et al., Cancer Res. 55:6045 (1995); Duan et al., ICE-LAP3, a novel mammalian homolog of the *Caenorhabditis elegans* cell death protein CED-3 is activated during Fas- and tumor necrosis factor-induced apoptosis, J. Biol. Chem. in press (1996)). Nicholson, supra.

However, it would be desirable to identify other mammalian (including human) ICE/CED-3 like proteases.

SUMMARY OF THE INVENTION

In accordance with the present invention, polynucleotides encoding a novel protease, FMH-1, and other related proteins are disclosed. "FMH-1" is used throughout the present specification to refer to both proteins and polynucleotides encoding those proteins and to refer to proteins and polynucleotides from all mammalian species.

In certain embodiments, the present invention provides for an isolated polynucleotide comprising a nucleotide sequence selected from the group consisting of:

(a) the nucleotide sequence of SEQ ID NO:1 from nucleotide 121 to nucleotide 1683;

(b) a nucleotide sequence capable of hybridizing to a nucleic acid sequence specified in (a);

(c) a nucleotide sequence encoding the amino acid sequence of SEQ ID NO:2 and varying from the sequence of the nucleotide sequence specified in (a) as a result of degeneracy of the genetic code;

(d) a nucleotide sequence comprising a fragment of (a) which encodes an amino acid sequence comprising amino acids 399 to 403 of SEQ ID NO:2;

(e) a nucleotide sequence comprising a fragment of (a) which encodes an amino acid sequence comprising amino acids 20 to 95 of SEQ ID NO:2; and (f) an allelic variant of the nucleotide sequence specified in (a). In preferred embodiments, the nucleotide sequence encodes for a protein having an activity selected from the group consisting of FMH-1 protease activity and adaptor binding activity. In other embodiments, the nucleotide sequence is operably linked to an expression control sequence. Preferably, the polynucleotide encodes a human FMH-1 protein. Particularly preferred embodiments include polynucleotides comprising the nucleotide sequence of SEQ ID NO:1 from nucleotide 121 to nucleotide 1683; a fragment of such sequence which encodes an amino acid sequence comprising amino acids 399 to 403 of SEQ ID NO:2; and a fragment of such sequence which encodes an amino acid sequence comprising amino acids 20 to 95 of SEQ ID NO:2.

The invention also provides for a host cell transformed with such polynucleotides, including mammalian cells. A process is also provided for producing an FMH-1 protein, said process comprising: (a) growing a culture of the host cell of the invention in a suitable culture medium; and (b) purifying the FMH-1 protein from the culture. Proteins produced according to such processes are also provided.

Pharmaceutical compositions are also provided comprising such polynucleotides and a pharmaceutically acceptable carrier. In preferred embodiments, the polynucleotide is contained in a vector suitable for gene therapy and/or the composition further comprises agents capable of increasing the uptake of said polynucleotide by cells.

The invention further provides an isolated FMH-1 protein comprising an amino acid sequence selected from the group consisting of:

(a) the amino acid sequence of SEQ ID NO:2;

(b) fragments of (a) having FMH-1 protease activity; and (c) fragments of (a) having adaptor binding activity.

Preferred embodiments include proteins comprising the amino acid sequence of SEQ ID NO:2, proteins comprising amino acids 399 to 403 of SEQ ID NO:2; and proteins comprising amino acids 20 to 95 of SEQ ID NO:2. Pharmaceutical compositions comprising such proteins and a pharmaceutically acceptable carrier are also provided.

The present invention also provides compositions comprising an antibody which specifically reacts with an FMH-1 protein of the invention.

The invention also provides for methods of treating conditions associated with excessive or insufficient apoptosis by administering to a mammalian subject a therapeutically effective amount of a pharmaceutical composition comprising an FMH-1 protein (as protein or in the form of a polynucleotide, for example, through gene therapy).

DETAILED DESCRIPTION OF PREFERRED EMBODIMENTS

The inventors of the present application have identified and provided a polynucleotide encoding a novel ICE/CED-3 like protease designated "FMH-1". SEQ ID NO:1 provides the nucleotide sequence of a cDNA encoding the human FMH-1 protein. SEQ ID NO:2 provides the amino acid sequence of the human FMH-1 protease.

Amino acids 331 to 472 of SEQ ID NO:2 show substantial homology/identity with other ICE/CED-3 like proteases and includes the domain responsible for protease activity (including the QACQG motif at amino acids 399 to 403). Amino acids 20 to 95 of SEQ ID NO:2 show significant homology to the adaptor protein binding domain of FADD protein (Fas-associating protein with death domain) (amino acids 1–86 of FADD) (see, Chinnaiyan et al., Cell 81:505 (1995)). It is believed that this domain in FMH-1 also constitutes an adaptor protein binding domain.

FMH-1 proteins comprising only one or several domains or portions thereof may also be produced. Any forms of FMH-1 protein of less than full length are encompassed within the present invention and may be produced by expressing a corresponding fragment of the polynucleotide encoding the FMH-1 protein (such as SEQ ID NO: 1). These corresponding polynucleotide fragments are also part of the present invention. Modified polynucleotides as described above may be made by standard molecular biology techniques, including site-directed mutagenesis methods which are known in the art or by the polymerase chain reaction using appropriate oligonucleotide primers.

For the purposes of the present invention, a protein has "FMH-1 protease activity" when it is capable of proteolysis in a manner characteristic of ICE/CED-3 like proteases. Protease activity of an FMH-1 protein can be measured by any of the assay methods reported in the references cited above relating to cloning and characterization of such proteases.

For the purposes of the present invention, a protein has "adaptor binding activity" when it is capable of binding to adaptor proteins in a manner characteristic of ICE/CED-3 like proteases or FADD. Binding activity of an FMH-1 protein can be measured by any of the assay methods reported in the references cited above relating to cloning and characterization of such proteases.

FMH-1 protein or fragments thereof having FMH-1 protease activity may be fused to carrier molecules such as immunoglobulins. For example, an FMH-1 protein may be fused through "linker" sequences to the Fc portion of an immunoglobulin.

The invention also encompasses allelic variations of the nucleotide sequence as set forth in SEQ ID NO:1, that is, naturally-occurring alternative forms of the isolated polynucleotide of SEQ ID NO:1 which also encode proteins having FMH-1 protease activity. Also included in the invention are isolated polynucleotides which hybridize to the nucleotide sequence set forth in SEQ ID NO:1 under highly stringent (0.2×SSC at 65° C.), stringent (e.g. 4×SSC at 65° C. or 50% formamide and 4×SSC at 42° C.), or relaxed (4×SSC at 50° C. or 30–40% formamide at 42° C.) conditions. Isolated polynucleotides which encode FMH-1 protein but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications which enhance FMH-1 protease activity, half-life or production level are also included in the invention.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the FMH-1 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the FMH-1 protein is expressed by a host cell which has been transformed (transfected) with the ligated polynucleotide/expression control sequence.

A number of types of cells may act as suitable host cells for expression of the FMH-1 protein. Any cell type capable of expressing functional FMH-1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12 or C2C12 cells.

The FMH-1 protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference. Soluble forms of the FMH-1 protein may also be produced in insect cells using appropriate isolated polynucleotides as described above.

Alternatively, the FMH-1 protein may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium,* or any bacterial strain capable of expressing heterologous proteins.

The FMH-1 protein of the invention may also be expressed as a product of transgenic animals, e.g., as a component of the milk of transgenic cows, goats, pigs, or sheep which are characterized by somatic or germ cells containing a polynucleotide sequence encoding the FMH-1 protein.

The FMH-1 protein of the invention may be prepared by growing a culture transformed host cells under culture conditions necessary to express the desired protein. The resulting expressed protein may then be purified from the culture medium or cell extracts. Soluble forms of the FMH-1 protein of the invention can be purified from conditioned media. Membrane-bound forms of FMH-1 protein of the invention can be purified by preparing a total membrane fraction from the expressing cell and extracting the membranes with a non-ionic detergent such as Triton X-100. The FMH-1 protein can be purified using methods known to those skilled in the art. For example, the FMH-1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the FMH-1 protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the FMH-1 protein. Some or all of the foregoing purification steps, in various combinations or with other known methods, can also be employed to provide a substantially purified isolated recombinant protein.

FMH-1 proteins can also be purified by affinity chromatography on resins linked with peptides which are, or mimic, substratees for FMH-1, including without limitation targets of proteolysis and adatpro proteins.

Preferably, the isolated FMH-1 protein is purified so that it is substantially free of other mammalian proteins.

FMH-1 introduced by gene therapy may be used for inducing apoptosis in target cell populations. Fragments of the protein, again introduced by gene therapy, may either induce or inhibit apoptosis in target cell populations. FMH-1 may be used as a target for peptide mimetics or small molecule inhibitors which may induce or inhibit apoptosis depending on which region of the molecule they bind. Induction or inhibition of apoptosis by the use of FMH-1, mimetics or inhibitors can be used to treat conditions discussed above in which excessive or insufficient apoptosis is implicated. The inhibition of apoptosis may also be used to enhance an immune reaction to weakly stimulatory antigen.

Polynucleotides of the invention, including polynucleotides encoding FMH-1 proteins, can be used in gene therapy in accordance with known methods. The polynucleotide can be introduced as naked DNA, in a viral vector or other suitable vector known in the art. Suitable methods include without limitation those described in WO95/26718, WO96/10038, WO93/19183, WO95/20660, U.S. Pat. No. 5,264,618, U.S. Pat. No. 5,459,127, WO90/11092, WO90/14074, WO91/16024, WO94/16716, WO89/01973 and WO93/14778.

Isolated FMH-1 proteins, purified from cells or recombinantly produced, may be used as a pharmaceutical composition when combined with a pharmaceutically acceptable carrier. Such a composition may contain, in addition to FMH-1 protein and carrier, diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical compositions may also contain other additional active factors or agents. Such additional factors and/or agents may be included in the pharmaceutical composition to produce a synergistic effect with isolated FMH-1 protein, or to minimize side effects caused by the isolated FMH-1 protein.

The pharmaceutical composition of the invention may be in the form of a liposome in which isolated FMH-1 protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Administration of isolated FMH-1 protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated FMH-1 protein is administered orally, isolated FMH-1 protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated FMH-1 protein, and preferably from about 25 to 90% isolated FMH-1 protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated FMH-1 protein, and preferably from about 1 to 50% isolated FMH-1 protein.

When a therapeutically effective amount of isolated FMH-1 protein is administered by intravenous, cutaneous or subcutaneous injection, isolated FMH-1 protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated FMH-1 protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of isolated FMH-1 protein in the pharmaceutical composition of the present invention will depend upon the nature and severity of the condition being treated, and on the nature of prior treatments which the patient has undergone. Ultimately, the attending physician will decide the amount of isolated FMH-1 protein with which to treat each individual patient. Initially, the attending physician will administer low doses of isolated FMH-1 protein and observe the patient's response. Larger doses of isolated FMH-1 protein may be administered until the optimal therapeutic effect is obtained for the patient, and at that point the dosage is not generally increased further. It is contemplated that the various pharmaceutical compositions used to practice the method of the present invention should contain about 0.1 µg to about 100 mg of isolated FMH-1 protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated FMH-1 protein will be in the range of 12 to 24 hours of continuous intravenous administration. Ultimately the attending physician will decide on the appropriate duration of intravenous therapy using the pharmaceutical composition of the present invention.

Isolated FMH-1 protein of the invention may also be used to immunize animals to obtain polyclonal and monoclonal antibodies which specifically react with the FMH-1 protein and which may inhibit ligand binding to the FMH-1. Such antibodies may be obtained using the entire FMH-1 protein as an immunogen, or by using fragments of FMH-1 protein such as the soluble mature FMH-1 protein. Smaller fragments of the FMH-1 protein may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Neutralizing or non-neutralizing antibodies (preferably monoclonal antibodies) binding to FMH-1 protein may also be useful therapeutics in the treatment of conditions described above. These neutralizing monoclonal antibodies are capable of blocking the ligand binding to the FMH-1 protein.

EXAMPLE 1

Isolation of FMH-1 cDNA

A partial clone for FMH-2 was isolated from a cDNA library made from RNA isolated from stimulated human peripheral blood mononuclear cells using methods as described in Maniatis, et al. The sequence from this clone was found to be homologous to another partial clone (here called FMH-1) from the EST/IMAGE consortium (T96912). 5' RACE was performed on a cDNA library (Clontech) from unstimulated human peripheral blood mononuclear cells using the Advantage PCR cDNA kit (Clontech) to obtain a full length clone for FMH-1. Comparison of this sequence to the sequence of the original partial IMAGE clone confirmed identity and that the isolated cDNA was full length.

The FMH-1 cDNA was deposited with ATCC on Jun. 26, 1996 at accession number 98086.

The sequence of FMH-1 shows regions of homology to FADD (Fas-associating protein with death domain) and to ICE (Interleukin-1 beta Converting Enzyme)-like enzymes. This suggests this protein is involved in linking Fas and TNF receptor adaptor proteins to the proteases in the signaling pathway leading to apoptosis (programmed cell death) (see, for example, Nicholson, Nature Biotechnology 14:297 (1996)).

All patent and literature references cited herein are incorporated by reference as if fully set forth.

What is claimed is:

1. An isolated protein comprising the amino acid sequence of SEQ ID NO:2.

* * * * *